(12) United States Patent
Cooper

(10) Patent No.: US 9,456,839 B2
(45) Date of Patent: Oct. 4, 2016

(54) SCISSOR BIAS FOR DIRECT PULL SURGICAL INSTRUMENT

(75) Inventor: Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 791 days.

(21) Appl. No.: 12/910,634

(22) Filed: Oct. 22, 2010

(65) Prior Publication Data

US 2011/0313449 A1    Dec. 22, 2011

Related U.S. Application Data

(60) Provisional application No. 61/356,551, filed on Jun. 18, 2010.

(51) Int. Cl.
*A61B 17/28* (2006.01)
*A61B 17/3201* (2006.01)
*A61B 17/29* (2006.01)

(52) U.S. Cl.
CPC ........... *A61B 17/3201* (2013.01); *A61B 34/30* (2016.02); *A61B 34/71* (2016.02); *A61B 17/28* (2013.01); *A61B 17/2804* (2013.01); *A61B 17/2816* (2013.01); *A61B 2017/294* (2013.01); (Continued)

(58) Field of Classification Search
CPC  A61B 17/3201; A61B 10/02; A61B 18/085; A61B 18/1445; A61B 2018/1457; A61B 2018/146; A61B 10/06; A61B 17/320016; A61B 17/28; A61B 17/2816; A61B 2018/0225; A61B 17/2804; A61B 17/282; A61B 2017/2926

USPC ........... 606/48, 51, 170, 174, 205, 206, 208; 600/564

See application file for complete search history.

(56) References Cited

U.S. PATENT DOCUMENTS

| 2,592,484 | A |   | 4/1952 | Smith |             |
|-----------|---|---|--------|-------|-------------|
| 5,290,309 | A | * | 3/1994 | Kothe | A61B 17/2833 |
|           |   |   |        |       | 606/207     |

(Continued)

FOREIGN PATENT DOCUMENTS

| CN | 1163558 A   | 10/1997 |
|----|-------------|---------|
| EP | 0887046 A2  | 12/1998 |

(Continued)

OTHER PUBLICATIONS

PCT/US2011/039067 Invitation to Pay Additional Fees with Partial International Search Report, mailed Oct. 10, 2011, 4 pages.

(Continued)

*Primary Examiner* — Diane Yabut

(57) ABSTRACT

A surgical end effector includes a clevis having a first end to be supported by an elongated tube-like member and two jaws, each having a pivot portion and a working portion. The pivot portions are rotatably coupled to the clevis by two spaced apart pivots. The working portions may include a cutting edge that provide a shearing action as the first and second jaws rotate about their respective pivots. The pivot portion and the working portion of each jaw may be on opposite sides of a bisecting plane. A flexible cable or wire may be coupled to each jaw and extend through a guide way in the other jaw, between the first and second pivots, and through the first end of the clevis. One or more springs may urge the working portions together. A rocking pin pivotally supported by the clevis may constrain the jaws to have opposite motions.

38 Claims, 4 Drawing Sheets

(52) U.S. Cl.
CPC  *A61B 2017/2926* (2013.01); *A61B 2017/2937* (2013.01); *A61B 2017/2939* (2013.01); *Y10T 29/49826* (2015.01)

(56) References Cited

U.S. PATENT DOCUMENTS

| | | | | |
|---|---|---|---|---|
| 5,312,434 | A | * | 5/1994 | Crainich ............... 606/207 |
| 5,575,805 | A | | 11/1996 | Li |
| 6,168,605 | B1 | | 1/2001 | Measamer et al. |
| 6,206,903 | B1 | | 3/2001 | Ramans |
| 6,840,938 | B1 | * | 1/2005 | Morley et al. ............ 606/51 |
| 7,648,519 | B2 | | 1/2010 | Lee et al. |
| 2009/0259248 | A1 | | 10/2009 | Ganter et al. |
| 2009/0281561 | A1 | | 11/2009 | Kessler |
| 2011/0144678 | A1 | * | 6/2011 | Slater .................... 606/170 |

FOREIGN PATENT DOCUMENTS

| | | |
|---|---|---|
| WO | WO-9610957 A1 | 4/1996 |
| WO | WO9610957 A1 | 4/1996 |

OTHER PUBLICATIONS

PCT/US2011/039067 International Search Report and Written Opinion of the International Searching Authority, mailed Nov. 30, 2011, 15 pages.

Office Action dated Jun. 21, 2012 for U.S. Appl. No. 12/702,200.

Jean Vertut and Philippe Coiffet; Teleoperation and Robotics, Evolution and Development; vol. 3A, Robot Technology; English Translation by Prentice-Hall, Inc. 1986.

Office Action mailed Apr. 14, 2015 for Chinese Application No. 2011829424 filed Jun. 3, 2011, 13 pages.

* cited by examiner

SCISSOR BIAS FOR DIRECT PULL SURGICAL INSTRUMENT

CROSS REFERENCE TO RELATED APPLICATIONS

This application claims the benefit pursuant to 35 U.S.C. 119(e) of U.S. Provisional Application No. 61/356,551, filed Jun. 18, 2010, which application is specifically incorporated herein, in its entirety, by reference.

BACKGROUND

1. Field

Embodiments of the invention relate to the field of surgical instruments; and more specifically, to surgical shears supported by an elongated tube-like member intended for use in minimally invasive surgeries.

2. Background

Minimally invasive surgery (MIS) (e.g., endoscopy, laparoscopy, thoracoscopy, cystoscopy, and the like) allows a patient to be operated upon through small incisions by using surgical instruments supported by an elongated tube-like member introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a scissors, a forceps, a clamp, a needle grasper, or the like at one end of an elongate tube. An actuator that provides the actuating forces to control the end effector is coupled to the other end of the elongate tube. A means of coupling the actuator forces to the end effector runs through the elongate tube. To minimize the size of incision needed for the instrument access port, the elongate tube is generally of a small diameter, preferably about 6 millimeters. Thus, it is necessary that the means of coupling the actuator forces to the end effector be compact.

It may be desirable that the elongate tube be somewhat flexible to allow the surgical instrument to adapt to the geometry of the surgical access path. In some cases, the elongate tube may be articulated to provide access to a surgical site that is not directly in line with the surgical access port. It may be desirable to use wires as the means of coupling the actuator forces to the end effector because of the flexibility they provide and because of the ability of a wire to transmit a significant force, a substantial distance, through a small cross-section. However, an unsupported wire is only able to transmit a force in tension. Thus it is generally necessary to provide two wires to transmit a bidirectional actuating force. This doubles the cross-section required for the wires to pass through the elongate tube.

The wires need to have sufficient strength to provide the tension necessary to create the required forces provided by the end effector. The more tension that is required, the larger the wire cross-section must be. Inefficiencies in converting wire tension into end effector forces increases the tension, and hence the cross-section, required. Increases in the cross-section, whether because of a greater number of wires or a larger cross-section of the individual cables, increases the effect of bending the cable, such as when is passes through an articulated wrist joint, on the force being delivered by the cable. This can cause changes in the closing force of a surgical end effector as the end effector is moved by an articulated wrist assembly that supports the end effector.

For surgical end effectors having two working parts that open and close relative to one another, such as the two blades of a pair of shears, it can be advantageous to route the force applying wires along the longitudinal axis of the tube and surgical end effector, continuing through the surgical end effector, around one of the two working parts, and then fixing the wire to the other working part. However, this is difficult with a conventional pair of shears that provides a fixed pivot point on the longitudinal axis of the surgical end effector joining the two cutting blades.

In view of the above, it would be desirable to provide a pair of surgical shears intended for use in minimally invasive surgeries that allows bidirectional actuating forces to be transmitted to the shears by wires routed along a longitudinal axis of an elongate tube and through the surgical shears.

SUMMARY

A surgical end effector includes a clevis having a first end to be supported by an elongated tube-like member and two jaws, each having a pivot portion and a working portion. The pivot portions are rotatably coupled to the clevis by two spaced apart pivots. The working portions may include a cutting edge that provide a shearing action as the first and second jaws rotate about their respective pivots. The pivot portion and the working portion of each jaw may be on opposite sides of a bisecting plane. A flexible cable or wire may be coupled to each jaw and extend through a guide way in the other jaw, between the first and second pivots, and through the first end of the clevis. One or more springs may urge the working portions together. A rocking pin pivotally supported by the clevis may constrain the jaws to have opposite motions.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
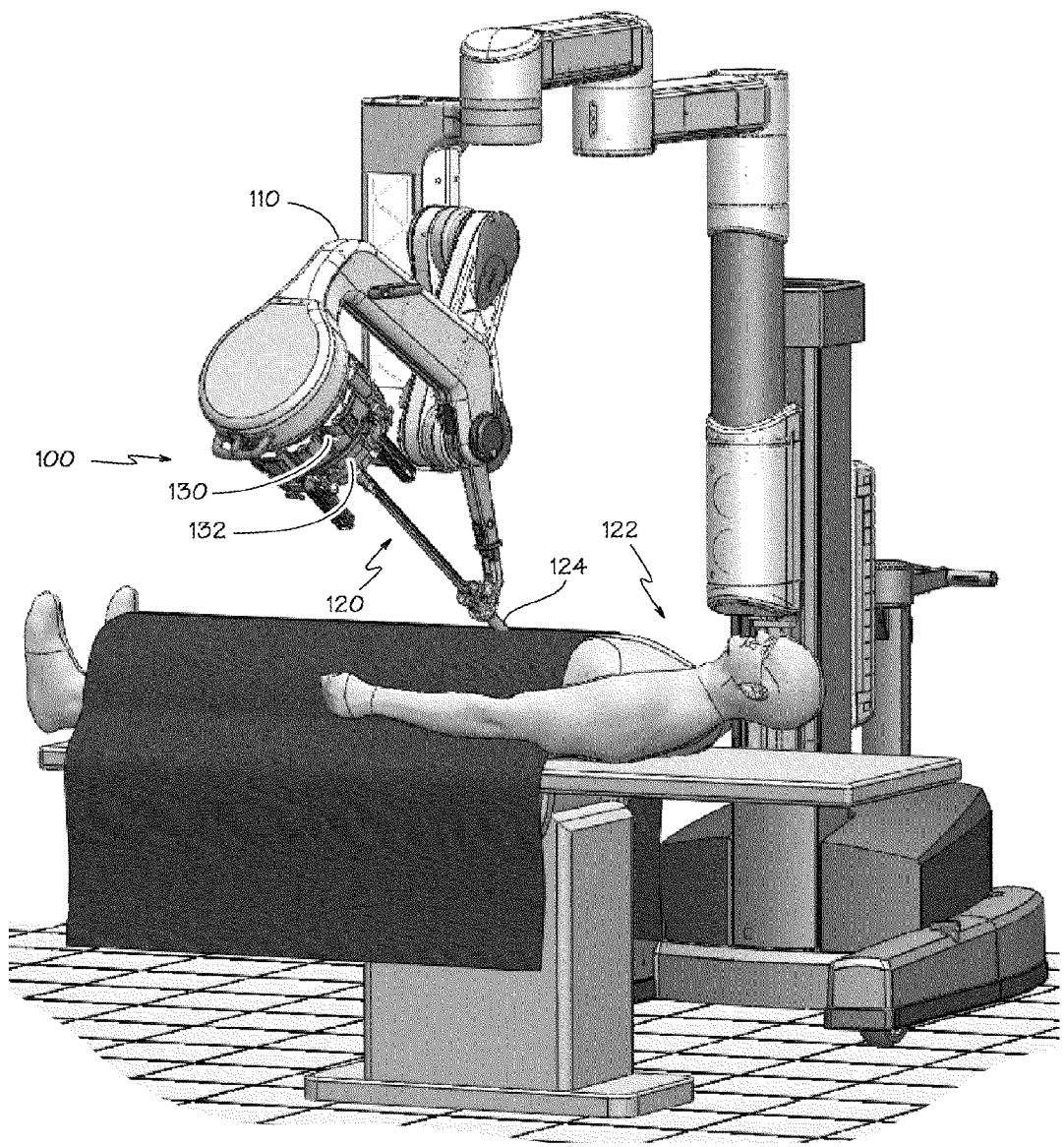
FIG. 1 is a simplified perspective view of a robotic surgical system with a robotically controlled surgical instrument inserted through a port in a patient's abdomen.

FIG. 1 is a simplified perspective view of a robotic surgical system 100, in accordance with embodiments of the present invention. The system 100 includes a support assembly 110 mounted to or near an operating table supporting a patient's body 122. The support assembly 110 supports one or more surgical instruments 120 that operate on a surgical site 126 within the patient's body 122.

The term "instrument" is used herein to describe a device configured to be inserted into a patient's body and used to carry out surgical procedures. The instrument includes a surgical tool, such as a forceps, a needle driver, a shears, a bipolar cauterizer, a tissue stabilizer or retractor, a clip applier, an anastomosis device, and the like. The surgical tool used with embodiments of the invention preferably provides a scissors or shears in which one cutting edge of the tool opens and closes relative to another cutting edge to cut with a shearing action.

The simplified perspective view of the system 100 shows only a single instrument 120 to allow aspects of the invention to be more clearly seen. A functional robotic surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional robotic surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control servo motors which, in turn, control the articulation of the surgical assembly. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide cannula 124, e.g., a single port in the patient's abdomen. A functional robotic surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a robotic positioning system for positioning the distal end 126 of the entry guide 124 at the desired target surgical site. The robotic positioning system may be provided in a variety of forms, such as a serial link arm having multiple degrees of freedom (e.g., six degrees of freedom) or a jointed arm that provides a remote center of motion (due to either hardware or software constraints) and which is positioned by a setup joint mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the robotic instrument manipulator 130. The robotic manipulator includes a coupler 132 to transfer controller motion from the robotic manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
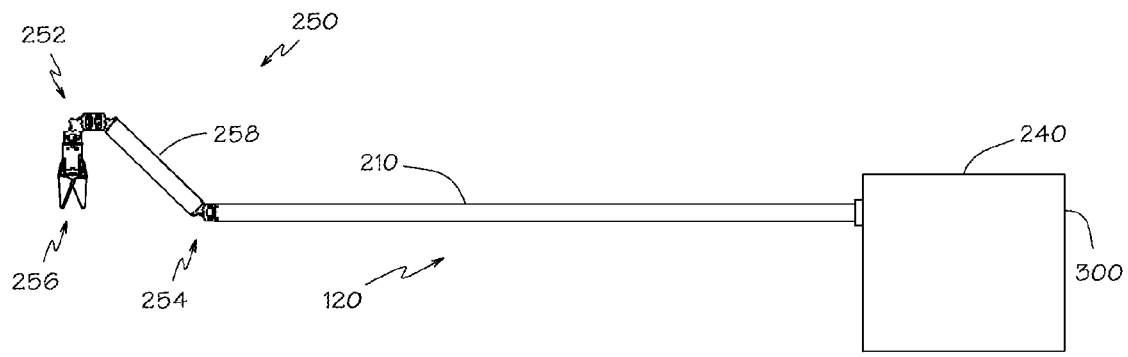
FIG. 2 is a plan view of a surgical instrument for use with a robotic manipulator.

FIG. 2 is a plan view of an illustrative embodiment of the surgical instrument 120, comprising a distal portion 250 and a proximal control mechanism 240 coupled by an elongate tube 210. The surgical instrument 120 preferably provides a cutting means 256 which is supported by the elongated tube-like member 210 which member permits surgical procedures to be undertaken in relatively confined areas. The distal portion 250 of the surgical instrument 120 preferably provides shears 256 as an end effector. In the embodiment shown, the shears 256 are coupled to the elongate tube 210 by two articulated sections, a "wrist" 252 and a "joggle joint" 254, coupled by a tubular section 258 that allow the position and orientation of the surgical tool to be manipulated.

Figure 3:
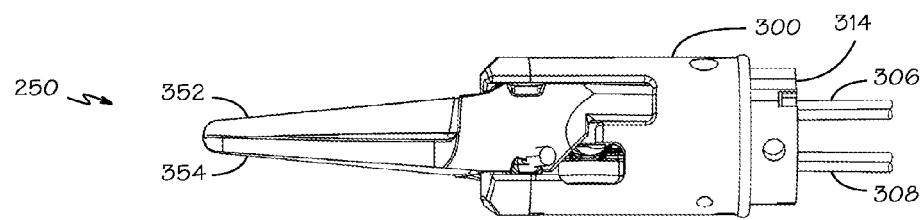
FIG. 3 is a side view of a surgical end effector.
Figure 4:
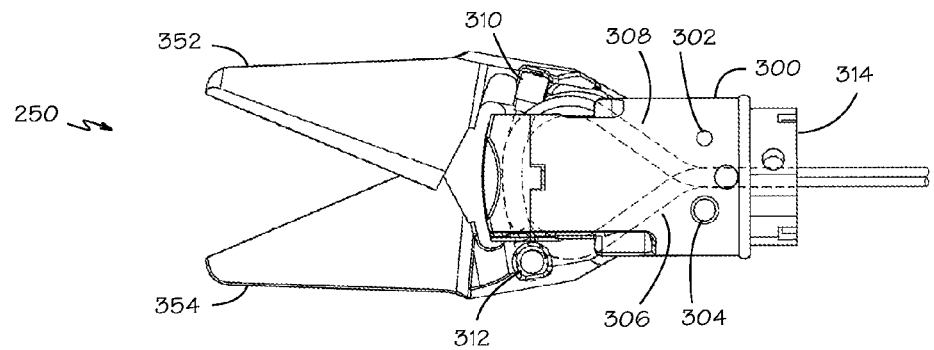
FIG. 4 is a front view of the surgical end effector of FIG. 3.
Figure 5:
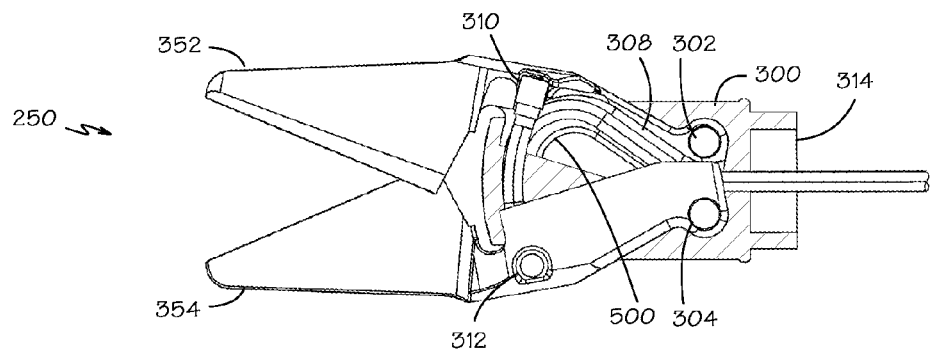
FIG. 5 is a front view of the surgical end effector of FIG. 3 with an upper portion removed to allow certain details to be seen more clearly.
Figure 6:
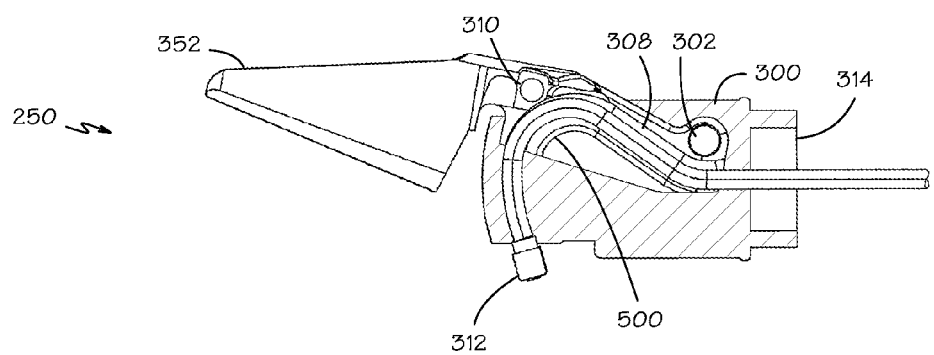
FIG. 6 is a front view of the surgical end effector of FIG. 3 with additional portions removed to allow additional details to be seen more clearly.

FIGS. 3 through 6 show an embodiment of a surgical end effector 250 that provides a pair of surgical shears or scissors that cut with a bypass shearing action. FIG. 3 shows a side view of the surgical end effector 250. FIG. 4 shows a top view of the surgical end effector 250. FIG. 5 shows a top view of the surgical end effector 250 with an upper portion removed to allow certain details to be seen more clearly. FIG. 6 shows a top view of the surgical end effector 250 with additional parts removed to allow additional details to be seen more clearly.

The surgical end effector 250 includes a clevis 300 that pivotally supports the first jaw 352 and the second jaw 354. A first pivot 302 couples the first jaw 352 to the clevis 300. A second pivot 304 couples the second jaw 354 to the clevis 300. The second pivot 304 is spaced apart from the first pivot 302.

A first flexible cable or wire 306 is coupled to the first jaw 352 by a first fitting 310 crimped to the end of the cable. The first wire 306 extends through a guide way in the second jaw 354, between the first 302 and second 304 pivots, and through a first end 314 of the clevis 300 that is supported by the articulated sections of the elongate tube 210. A second wire 308 is coupled to the second jaw 354 by a second fitting 312 crimped to the end of the cable. The second wire 308 extends through a guide way in the first jaw 352, between the first 302 and second 304 pivots, and through the first end 314 of the clevis 300. The first and second wires 306, 308 provide opening and closing forces to actuate the first and second jaws 352, 354.

As best seen in FIGS. 5 and 6, the guide way 500 guides the wire 308 along a curved path that changes the direction of the wire by roughly 90°. Each of the first and second jaws 352, 354 includes a face that is perpendicular to the first and second pivots 302, 304. The guide way includes a groove 500 in the face. In the embodiment shown, the wire is stranded to increase the flexibility and facilitate the ability of the wire to follow the curved path. In other embodiments, a solid wire is used to provide greater strength for a given cross-section size of the wire.

In one embodiment, the surgical end effector further includes two liners. Each liner is coupled to a face of one of the jaws and fitted within the groove 500 that forms the guide way. Thus the guide ways include a portion of the liners. The liners reduce the friction as the wires 306, 308 slide within the guide ways. The liners also electrically isolate the wires 306, 308 from the jaw through which they slide.

The arrangement of the wires 306, 308 causes tension in each wire to apply a closing force to both jaws 352, 354. For example, when tension is applied to the second wire 308, the coupling 312 to the second jaw 354 will pull on the jaw to close it. At the same time, the tension applied to the second wire 308 will create a closing force on the first jaw 352 because of the forces created in the guide way as the second wire is turned by the guide way. Likewise, a compression force applied to each wire creates an opening force on both jaws 352, 354. This wire arrangement permits higher opening and closing forces to be generated by a more compact end effector.

Figure 7:
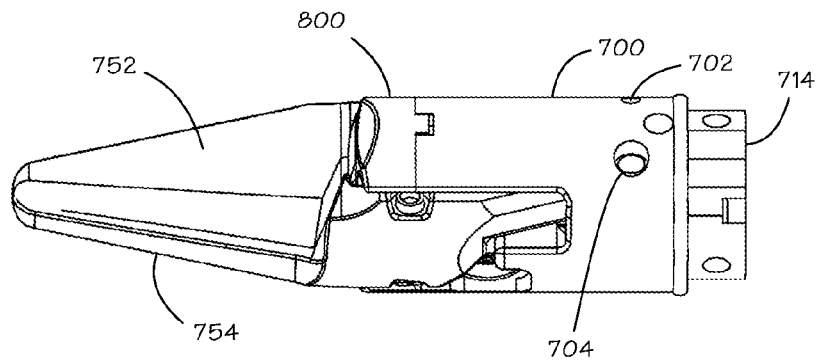
FIG. 7 is side view of another surgical end effector.
Figure 8:
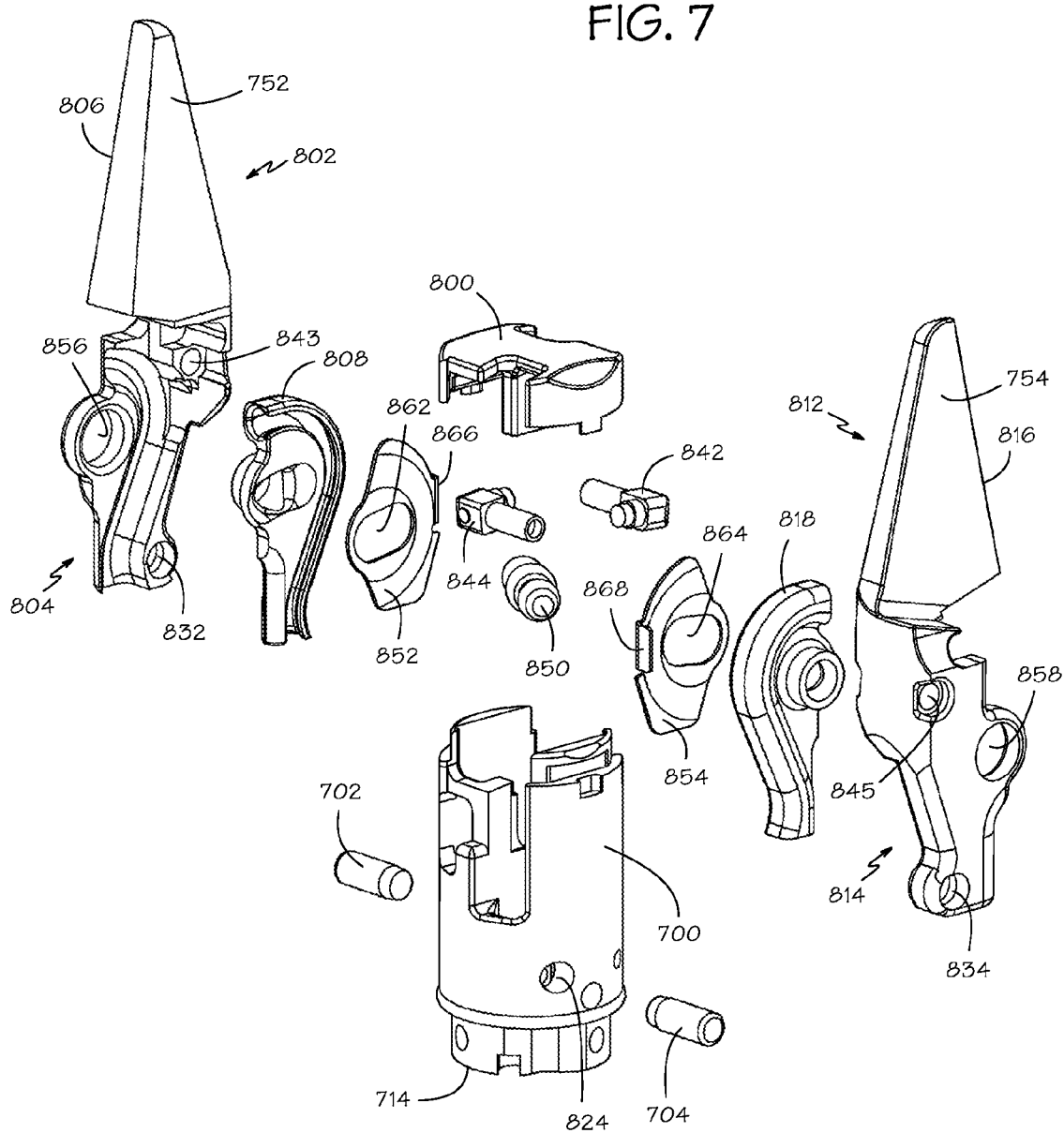
FIG. 8 is an exploded view of the surgical end effector of FIG. 7.

FIG. 7 shows a top view of the surgical end effector that embodies the invention. FIG. 8 shows an exploded view of the surgical end effector of FIG. 7.

A clevis 700 has a first end 714 to be supported by the elongated tube-like member 210. A first jaw 752 has a first pivot portion 804 and a first working portion 802 that comprises a first cutting edge 806. A first pivot 702 rotatably couples the first jaw 752 to the clevis 700. A second jaw 754 has a second pivot portion 814 and a second working portion 812 that comprises a second cutting edge 816 that bypasses the first cutting edge 806 to provide a shearing action. A second pivot 704 spaced apart from the first pivot 702 rotatably couples the second jaw 754 to the clevis 700. A cap 800 closes the end of the clevis 700 opposite the first end 714.

In the embodiment shown, the first and second pivots 702, 704 are in the form of cylindrical pins that are pressed into corresponding openings 824 in the clevis 700. The first and second pivots 702, 704 provide two parallel rotational axes that are spaced apart leaving the space around the central cylindrical axis of the clevis 700 open so the wires 306, 308 can extend through that portion of the clevis. Openings 832, 834 in the pivot portions 804, 814 of each of the jaws 752, 754 are rotatably supported by the pivots 702, 704.

A described above, a liner 808, 818 is inserted into a corresponding groove in a face of the pivot portion 804, 814 of each of the jaws 752, 754 to provide a guide way. A wire (not shown) is coupled to a fitting 842, 844, such as by crimping, that coupled to a corresponding opening 843, 845 in one of the jaws. The wire extends from the fitting 842, 844, through the guide way in the other jaw 754, 752, between the first and second pivots 702, 704, and through the first end 714 of the clevis 700.

To provide an effective shearing action by the first 806 and second 816 cutting edges as they bypass one another, it is necessary that the cutting edges bear against one another with a significant pressure. In the embodiment shown, a first spring 852 is coupled to the first pivot portion 804 and the clevis 700 and a second spring 854 is coupled to the second pivot portion and the clevis. The springs 852, 854 are in the form of cupped spring washers, sometime referred to as Belleville washers. The springs urge the pivot portions apart from one another. As will be further explained below, the pivot portions and the working portions are on opposite sides of a bisecting plane. Therefore as the pivot portions are urged apart, the working portions are urged together.

In other embodiments one spring may be used to bias the cutting edges together. In other embodiments more than two springs may be used to bias the cutting edges together. In some embodiments the jaws may be configured such that the springs urge both the pivot portions and the working portions together.

In the embodiment shown, a rocking pin 850 is pivotally supported by the clevis 700 and pivotally coupled to corresponding openings 856, 858 in the first and second jaws 752, 754 such that the rocking pin constrains the first and second jaws to have opposite motions. The rocking pin 850 passes through central openings 862, 864 in the springs 852, 854.

In the embodiment shown, tabs 866, 868 on each of the springs 852, 854 engage the jaws 752, 754 such that the springs rotate in unison with their respective jaws. In this way it is possible to use springs that are not circular so that their shape corresponds to the shape of the adjacent face of the jaw.

Figure 9:
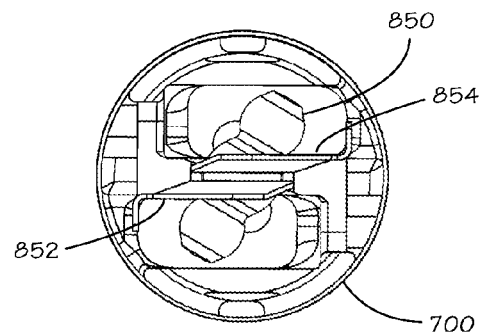
FIG. 9 is a top view of a portion of the surgical end effector of FIG. 7.

FIG. 9 is a view of the clevis 700 from the end that would be closed by the cap and opposite the first end. The relationship of the two spring washers 852, 854 to the clevis 700 may be more clearly seen in this view. The relationship of the rocking pin 850 to the clevis 700 may also be more clearly seen in this view.

Figure 10:
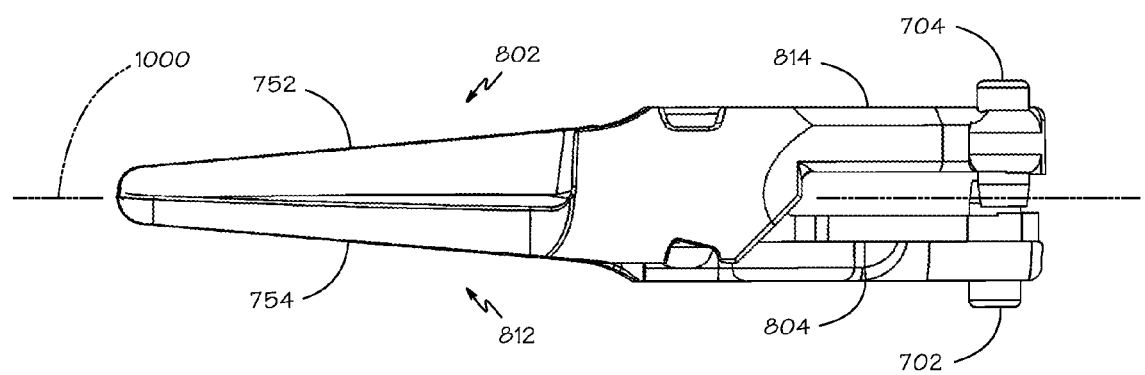
FIG. 10 is a side view of the jaw portion of the surgical end effector of FIG. 7.
Figure 11:
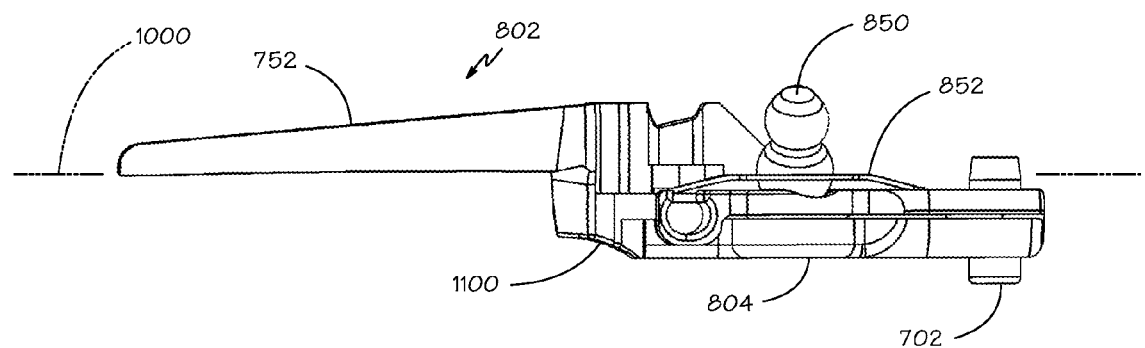
FIG. 11 is a side view of one jaw from the surgical end effector of FIG. 7.

FIG. 10 is a side view of the two jaws 752, 754 without the clevis. FIG. 11 is a side view of one the jaws 752 without the clevis. As suggested by the dashed line 1000, the pivot portions 804, 814 are on a first side of a bisecting plane that is perpendicular to an axis of rotation of the pivots 702, 704 and the working portions 802, 812 are on the opposite side of the bisecting plane.

Referring specifically to FIG. 11, the pivot portion 804 of the first jaw 752 is below the bisecting plane, which is perpendicular to the page of the drawing with the intersection of the bisecting plane and the page of the drawing suggested by the dashed line 1000. The working portion 802 of the first jaw 752 is above the bisecting plane. A coupling portion 1100 of the first jaw 752 passes through the bisecting plane to join the pivot portion 804 and the working portion 802. This cross-over structure of the jaws allows the biasing force of the springs to be applied adjacent the bisecting plane.

Application of the biasing force adjacent the bisecting plane may be advantageous because of the small size and cylindrical shape of the clevis which limits the space available. Application of the biasing force adjacent the bisecting plane urges the working portions 802, 812 of the two jaws 752, 754 toward one another and the pivot portions 804, 814 away from one another. The clevis 700 supplies an inward reaction force at the pivots 702, 704 to oppose the outward forces applied to the pivot portions 804, 814 of the two jaws 752, 754. The first end 714 of the clevis adjacent the pivots 702, 704 provides a complete cylindrical structure with the strength and rigidity to provide the inward reaction force without bending. The thinner structures of the clevis adjacent the cap 800 where portions of the clevis are cut away to receive the two jaws 752, 754 are not subject to bending forces from the biasing springs 852, 854.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A surgical end effector comprising:
   a clevis;
   a first jaw having a first pivot portion and a first working portion;
   a first pivot that rotatably couples the first pivot portion to the clevis such that the first jaw rotates about a first axis that is fixed relative to the clevis;
   a second jaw having a second pivot portion and a second working portion; and
   a second pivot that rotatably couples the second pivot portion to the clevis such that the second jaw rotates about a second axis that is fixed relative to the clevis, the second axis being parallel to and spaced apart from the first axis, the second jaw coupled to the clevis such that the first pivot portion is entirely on a first side of a bisecting plane that is perpendicular to the first and second axes of rotation, the second pivot portion is entirely on a second side of the bisecting plane opposite the first side, the first working portion is entirely on the second side of the bisecting plane, and the second working portion is entirely on the first side of the bisecting plane.

2. The surgical end effector of claim 1 further comprising:
   a first wire coupled to the first jaw, the first wire extending through a guide way in the second jaw, between the first and second axes of rotation, and through a first end of the clevis; and
   a second wire coupled to the second jaw, the second wire extending through a guide way in the first jaw, between the first and second axes of rotation, and through the first end of the clevis.

3. The surgical end effector of claim 1 further comprising a first spring coupled to the first pivot portion and the clevis, the first spring urging the first pivot portion away from the bisecting plane.

4. The surgical end effector of claim 3 further comprising a second spring coupled to the second pivot portion and the clevis, the second spring urging the second pivot portion away from the bisecting plane.

5. The surgical end effector of claim 1 further comprising a first spring coupled to the first and second pivot portions, the first spring urging the first and second pivot portions away from the bisecting plane.

6. The surgical end effector of claim 5 wherein the first spring comprises a cupped spring washer.

7. The surgical end effector of claim 6 wherein the first spring engages the first jaw such that the first spring rotates in unison with the first jaw.

8. The surgical end effector of claim 7 further comprising a rocking pin pivotally supported by the clevis and pivotally coupled to the first and second jaws such that the rocking pin constrains the first and second jaws to have opposite motions, the rocking pin passing through a central opening in the first spring.

9. The surgical end effector of claim 1 further comprising a first spring coupled to the first pivot portion and the clevis and a second spring coupled to the second pivot portion and the clevis to urge the pivot portions away from the bisecting plane.

10. The surgical end effector of claim 1 wherein the first and second working portions each include a cutting edge that provide a shearing action as the first and second jaws rotate about their respective pivots.

11. A method of making a surgical end effector, the method comprising:
   providing a clevis;
   providing a first jaw having a first pivot portion and a first working portion;
   rotatably coupling the first pivot portion to the clevis with a first pivot such that the first jaw rotates about a first axis that is fixed relative to the clevis;
   providing a second jaw having a second pivot portion and a second working portion; and
   rotatably coupling the second pivot portion to the clevis with a second pivot such that the second jaw rotates about a second axis that is fixed relative to the clevis, the second axis being parallel to and spaced apart from the first axis, the second jaw coupled to the clevis such that the first pivot portion is entirely on a first side of a bisecting plane that is perpendicular to the first and second axes of rotation, the second pivot portion is entirely on a second side of the bisecting plane opposite the first side, the first working portion is entirely on the second side of the bisecting plane, and the second working portion is entirely on the first side of the bisecting plane.

12. The method of claim 11 further comprising:
   coupling a first wire to the first jaw, the first wire extending through a guide way in the second jaw, between the first and second axes of rotation, and through a first end of the clevis; and
   coupling a second wire to the second jaw, the second wire extending through a guide way in the first jaw, between the first and second axes of rotation, and through the first end of the clevis.

13. The method of claim 11 further comprising coupling a first spring to the first pivot portion and the clevis, the first spring urging the first pivot portion away from the bisecting plane.

14. The method of claim 13 further comprising coupling a second spring to the second pivot portion and the clevis, the second spring urging the second pivot portion away from the bisecting plane.

15. The method of claim 11 further comprising coupling a first spring coupled to the first and second pivot portions, the first spring urging the first and second pivot portions away from the bisecting plane.

16. The method of claim 15 wherein the first spring comprises a cupped spring washer.

17. The method of claim 16 further comprising engaging the first spring with the first jaw such that the first spring rotates in unison with the first jaw.

18. The method of claim 17 further comprising pivotally supporting a rocking pin in the clevis, passing the rocking pin through a central opening in the first spring, and pivotally coupling the rocking pin to the first and second jaws such that the rocking pin constrains the first and second jaws to have opposite motions.

19. The method of claim 11 further comprising coupling a first spring to the first pivot portion and the clevis and coupling a second spring to the second pivot portion and the clevis to urge the pivot portions away from the bisecting plane.

20. The method of claim 11 wherein the first and second working portions each include a cutting edge that provide a shearing action as the first and second jaws rotate about their respective pivots.

21. A surgical end effector comprising:
   a clevis;
   a first jaw having a first pivot portion and a first working portion, the first pivot portion being entirely on a first side of a bisecting plane, the first working portion being entirely on a second side of the bisecting plane opposite the first side, the first working portion comprising a first cutting edge;
   a first pivot that rotatably couples the first jaw to the clevis such that the first jaw rotates about a first axis that is fixed relative to the clevis, the first axis being perpendicular to the bisecting plane;
   a second jaw having a second pivot portion and a second working portion, the second pivot portion being entirely on the second side of the bisecting plane, the second working portion being entirely on the first side of the bisecting plane, the second working portion comprising a second cutting edge that bypasses the first cutting edge to provide a shearing action in relation to the first cutting edge; and
   a second pivot that rotatably couples the second jaw to the clevis such that the second jaw rotates about a second axis that is fixed relative to the clevis, the second axis being perpendicular to the bisecting plane and parallel to and spaced apart from the first axis.

22. The surgical end effector of claim 21 further comprising:
   a first wire coupled to the first jaw, the first wire extending through a guide way in the second jaw, between the first and second axes of rotation, and through a first end of the clevis; and
   a second wire coupled to the second jaw, the second wire extending through a guide way in the first jaw, between the first and second axes of rotation, and through the first end of the clevis.

23. The surgical end effector of claim 21 further comprising a first spring coupled to the first pivot portion and the clevis, the first spring urging the first working portion toward the second working portion.

24. The surgical end effector of claim 23 further comprising a second spring coupled to the second pivot portion and the clevis, the second spring urging the second working portion toward the first working portion.

25. The surgical end effector of claim 21 further comprising a first spring coupled to the first and second pivot portions, the first spring urging the first pivot portion away from the second pivot portion and the first working portion toward the second working portion.

26. The surgical end effector of claim 25 wherein the first spring comprises a cupped spring washer.

27. The surgical end effector of claim 26 wherein the first spring engages the first jaw such that the first spring rotates in unison with the first jaw.

28. The surgical end effector of claim 27 further comprising a rocking pin pivotally supported by the clevis and pivotally coupled to the first and second jaws such that the rocking pin constrains the first and second jaws to have opposite motions, the rocking pin passing through a central opening in the first spring.

29. The surgical end effector of claim 21 further comprising a first spring coupled to the first pivot portion and the clevis and a second spring coupled to the second pivot portion and the clevis to urge the pivot portions away from the bisecting plane.

30. A method of making a surgical end effector, the method comprising:

provide a clevis;

providing a first jaw having a first pivot portion and a first working portion, the first pivot portion being entirely on a first side of a bisecting plane, the first working portion being entirely on a second side of the bisecting plane opposite the first side, the first working portion comprising a first cutting edge;

rotatably coupling the first jaw to the clevis with a first pivot such that the first jaw rotates about a first axis that is perpendicular to the bisecting plane and fixed relative to the clevis;

providing a second jaw having a second pivot portion and a second working portion, the second pivot portion being entirely on the second side of the bisecting plane, the second working portion being entirely on the first side of the bisecting plane, the second working portion comprising a second cutting edge that bypasses the first cutting edge to provide a shearing action in relation to the first cutting edge; and rotatably coupling the second jaw to the clevis with a second pivot such that the second jaw rotates about a second axis that is perpendicular to the bisecting plane and fixed relative to the clevis, the second axis being parallel to and spaced apart from the first axis.

31. The method of claim 30 further comprising:

coupling a first wire to the first jaw, the first wire extending through a guide way in the second jaw, between the first and second axes of rotation, and through a first end of the clevis; and coupling a second wire to the second jaw, the second wire extending through a guide way in the first jaw, between the first and second axes of rotation, and through the first end of the clevis.

32. The method of claim 30 further comprising coupling a first spring to the first pivot portion and the clevis, the first spring urging the first working portion toward the second working portion.

33. The method of claim 32 further comprising coupling a second spring to the second pivot portion and the clevis, the second spring urging the second working portion toward the first working portion.

34. The method of claim 30 further comprising coupling a first spring to the first and second pivot portions, the first spring urging the first pivot portion away from the second pivot portion and the first working portion toward the second working portion.

35. The method of claim 34 wherein the first spring comprises a cupped spring washer.

36. The method of claim 35 further comprising engaging the first spring with the first jaw such that the first spring rotates in unison with the first jaw.

37. The method of claim 36 further comprising pivotally supporting a rocking pin in the clevis, passing the rocking pin through a central opening in the first spring, and pivotally coupling the rocking pin to the first and second jaws such that the rocking pin constrains the first and second jaws to have opposite motions.

38. The method of claim 30 further comprising coupling a first spring to the first pivot portion and the clevis and coupling a second spring to the second pivot portion and the clevis to urge the pivot portions away from the bisecting plane.

* * * * *